United States Patent [19]

Cartmell et al.

[11] Patent Number: 5,674,523
[45] Date of Patent: Oct. 7, 1997

[54] SELF-ADHESIVE HYDROGEL WOUND DRESSING

[75] Inventors: James Vernon Cartmell, Xenia; Wayne R. Sturtevant, Centerville; Michael Lee Wolf, West Milton, all of Ohio

[73] Assignee: New Dimensions in Medicine, Inc., Dayton, Ohio

[21] Appl. No.: 523,009

[22] Filed: Sep. 1, 1995

[51] Int. Cl.⁶ .................................................. A61L 15/00
[52] U.S. Cl. ............................ 424/445; 424/443; 424/447
[58] Field of Search ............................ 424/443, 445, 424/447; 602/46, 47

[56] References Cited

U.S. PATENT DOCUMENTS

| | | | |
|---|---|---|---|
| 4,226,232 | 10/1980 | Spence | 128/156 |
| 4,377,160 | 3/1983 | Romaine | 128/156 |
| 4,657,006 | 4/1987 | Rawlings et al. | 128/156 |
| 5,059,424 | 10/1991 | Cartmell et al. | 424/443 |
| 5,336,209 | 8/1994 | Porzilli | 604/307 |
| 5,356,372 | 10/1994 | Donovan et al. | 602/58 |
| 5,406,945 | 4/1995 | Riazzi et al. | 128/641 |
| 5,423,737 | 6/1995 | Cartmell et al. | 602/57 |
| 5,429,592 | 7/1995 | Jensen | 602/59 |

*Primary Examiner*—Thurman K. Page
*Assistant Examiner*—Sharon Howard
*Attorney, Agent, or Firm*—Killworth, Gottman, Hagan & Schaeff, L.L.P.

[57] ABSTRACT

An elongated, self-adhesive wound dressing is provided which includes a hydrogel layer secured to a vapor permeable bacterial barrier layer. The vapor permeable barrier layer possesses sufficient porosity such that it readily adheres to the hydrogel layer without the need for an adhesive layer. The wound dressing is adapted to be wrapped around a portion of a patient's body and secured without the use of an adhesive.

11 Claims, 5 Drawing Sheets

SELF-ADHESIVE HYDROGEL WOUND DRESSING

BACKGROUND OF THE INVENTION

The present invention relates to wound dressings, and more particularly, to an elongated wound dressing containing a hydrogel material which can be wrapped around a portion of a patient's body without the use of an adhesive.

Skin wounds, such as open surgical wounds, stasis ulcers, and burns have long presented a medical challenge in keeping such wounds sterile and relatively dry. The accumulation of wound exudate, such as blood, pustulation, and other wound fluids in wound crevices, promotes growth of bacteria and other organisms which causes infection and delay the healing process. Such wound exudate may also cause maceration of tissue adjacent the wound and support infection thereof. Burn injuries, in particular, require a unique therapy and dressing because the physiologic functions of the skin are absent or, at best, materially impaired. Body fluids and their essential components are continuously lost, and the natural bacterial barrier characteristics of the skin are no longer functional.

There is a substantial body of prior art relating to wound and surgical dressings or packings for treating wounds, such as burns, stasis ulcers, and other high exudating wounds. In some instances, the wound dressing or packing may be designed to be only temporary, such as the use of gauze to absorb blood and other wound exudate. In others, the wound dressing is designed to be more permanent in nature, remaining in place for several hours or days during the healing process. In yet other instances, the wound dressing material is designed to be biodegradable and to break down over an extended period of time as a wound heals.

Aqueous moisture absorbing materials, such as a hydrogel material with a polyethylene glycol liquid curing agent, as disclosed in Spence, U.S. Pat. No. 4,226,232, have been used as dressings on a wound site, but cannot be sterilized by irradiation due to the formation of free radicals within the aqueous material. Another aqueous absorbing material used to absorb wound exudate is a hydrophilic polymer, as disclosed in Rawlings et al, U.S. Pat. No. 4,657,006. Rawlings et al discloses a wound dressing which comprises a hydrophilic polymer having moisture and vapor permeability characteristics. However, a problem with the Rawlings et al wound dressing is that the wound exudate absorbed by the hydrophilic polymer hardens or solidifies the polymer, allowing pockets to develop between the polymer and the wound, thereby providing an excellent environment for bacteria proliferation.

Further, many wound dressings in use are not made from transparent materials and thus, must be removed in order to check the healing progress of the wound. This may inhibit the healing process, as frequent removal and replacement of the bandage may destroy new cell tissue.

In recent years, hydrogel wound dressings have been developed which have been more effective in treating wounds without damaging the wound and without the problem of sterilization. One such wound dressing is disclosed in Cartmell et al, U.S. Pat. No. 5,059,424, and comprises a thin-film transparent layer including an adhesive layer on one side, and a hydrogel layer positioned in the center portion of the adhesive layer. The wound dressing is applied to the skin of a patient such that the hydrogel contacts the wound and the adhesive around the perimeter of the wound dressing adheres to the skin of the patient.

However, while such hydrogel wound dressings have been effective in absorbing wound exudate, the use of an adhesive to secure the dressing to the skin of a patient may cause irritation to patients having sensitive skin. The use of adhesives also presents a problem for burn sites, which typically have very little healthy skin to which such a dressing may be adhered. Further, the use of an adhesive adds to production costs.

Accordingly, there is a need in the art for a sterile wound dressing which is especially conducive for high exudating wounds such as burns and stasis ulcers, which may be applied to a portion of a patient's body without the use of an adhesive, and which permits visual inspection of the wound without removing the dressing from the wound.

SUMMARY OF THE INVENTION

The present invention meets those needs by providing a wound dressing which includes a hydrogel layer for absorbing wound exudate which is secured to a vapor permeable layer which protects the wound from bacterial invasion. The wound dressing is provided in an elongated form and is designed to be wrapped around a portion of a patient's body without the use of an adhesive.

According to one aspect of the present invention, an elongated, self-adhesive wound dressing is provided which is adapted to be wrapped around a portion of the patient's body so as to cover a wound. The wound dressing comprises a hydrogel layer having first and second sides, where the first side of the hydrogel layer is adapted to contact the skin of a patient. The wound dressing further includes a vapor permeable bacterial barrier layer having first and second sides, where the first side of the barrier layer is secured to the second side of the hydrogel layer.

The vapor permeable bacterial barrier layer is formed of a porous material having sufficient porosity such that the hydrogel layer impregnates and adheres to the barrier layer without the use of an adhesive layer. Preferably, the vapor permeable barrier layer has a porosity in the range of from about 30% to about 90%, and comprises a foam material including silica and a polyolefin.

In a preferred embodiment of the invention, the hydrogel layer is substantially transparent and the vapor permeable bacterial barrier layer includes at least one open area therein such that a wound can be viewed through the open area and the hydrogel. In one embodiment of the invention, the open area comprises a window. In an alternative embodiment, the open area comprises a gap in the barrier layer.

A transparent film is preferably adhered to at least a portion of the second side of the vapor permeable bacterial barrier layer such that the open area is covered by the transparent film. Preferably, the transparent film comprises polyurethane and is secured to the vapor permeable bacterial barrier layer with a pressure sensitive adhesive.

The wound dressing preferably further comprises a release liner releasably secured to the first side of the hydrogel layer for protection of the hydrogel layer prior to use.

A preferred method of applying the elongated wound dressing of the present invention includes the steps of peeling the release liner from the wound dressing to expose the hydrogel, and then placing the center portion of the wound dressing on the wound such that the exposed hydrogel contacts the wound. The respective first and second ends of the wound dressing are then gripped and the wound dressing is wrapped around a portion of the patient's body such that the first surface of the hydrogel contacts and adheres to the second surface of the vapor permeable bacterial barrier layer, thereby maintaining the wound dressing in position over the wound. Because the hydrogel readily adheres to the vapor permeable bacterial barrier layer, there is no need to use an adhesive to secure the wound dressing after it has been wrapped around the wound.

The hydrogel material directly contacts the wound where it creates a fluid absorbing, cushioned skin-like media to facilitate the healing process, while the vapor permeable layer permits the passage of water vapor and at the same time protects the wound from bacterial invasion. The wound dressing of the present invention can be manufactured to any desired length and is especially useful in the treatment of burns, stasis ulcers, and other high exudating wounds. The wound dressing may also function as an I.V. hold-down wrap in embodiments where the wound dressing includes a transparent window.

Accordingly, it is a feature of the present invention to provide a wound dressing containing a hydrogel material which is secured without an adhesive to a vapor permeable layer which provides bacterial protection to a wound. It is a further feature of the invention to provide an elongated wound dressing which may be wrapped around a patient's body and secured thereto without the use of an adhesive. These, and other features and advantages of the present invention will become apparent from the following detailed description, the accompanying drawings, and the appended claims.

DETAILED DESCRIPTION OF THE PREFERRED EMBODIMENTS

Figure 4:
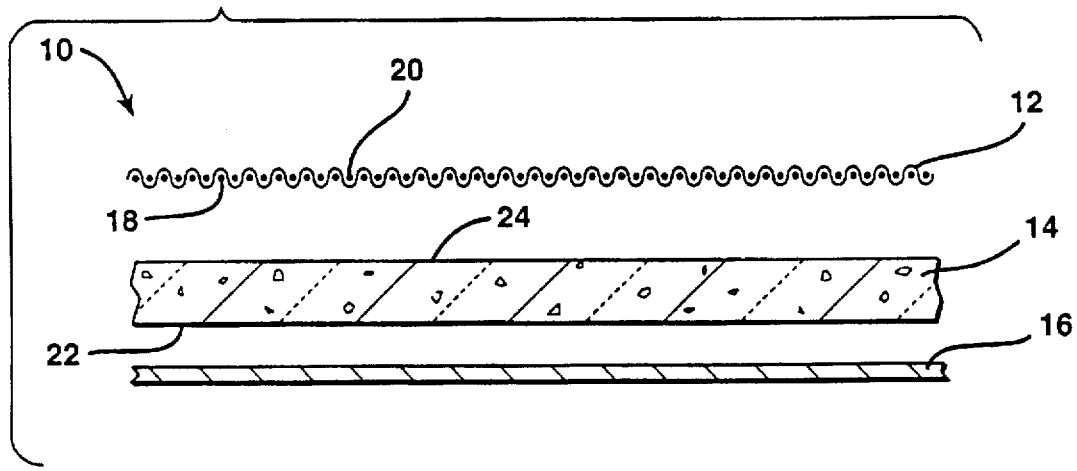
FIG. 4 is a cross-sectional view of the embodiment shown in FIG. 1.
Figure 5:
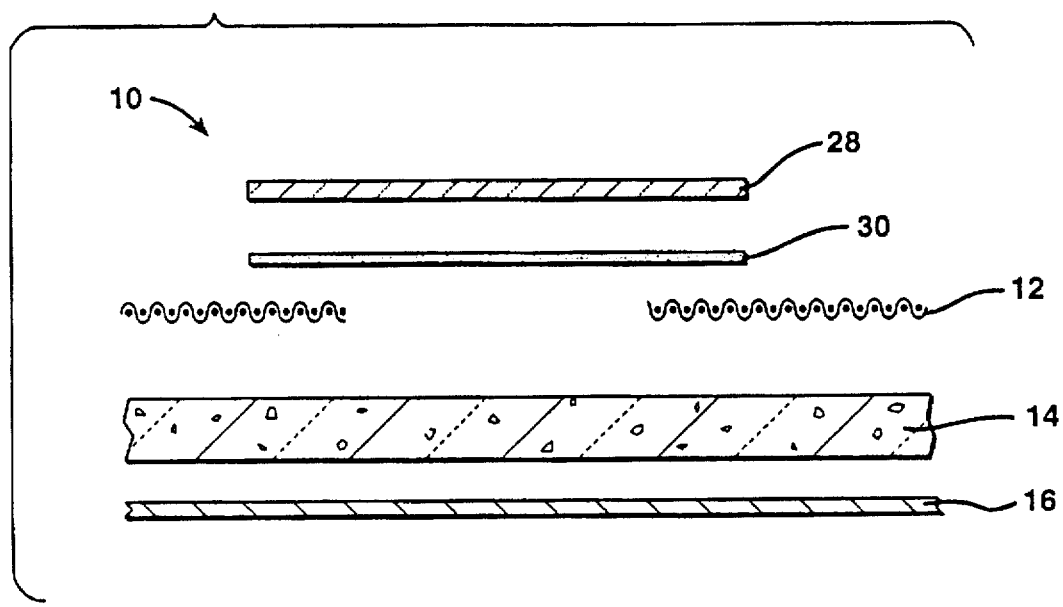
FIG. 5 is a cross-sectional View of the embodiments shown in FIGS. 2 and 3, taken along a line parallel to the elongated direction of the wound dressing.
Figure 6:
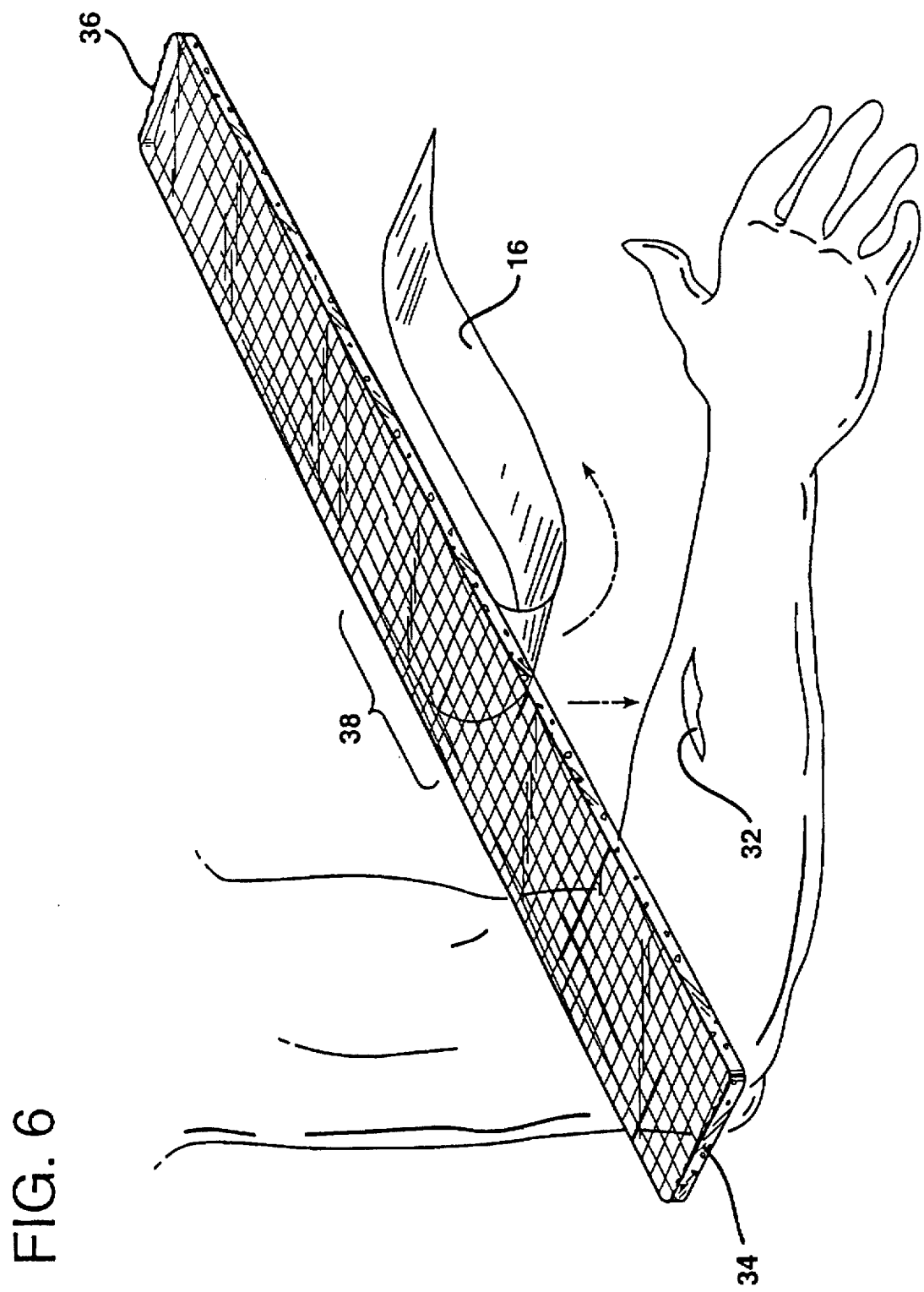
FIGS. 6 and 7 illustrate the preferred method of application of the wound dressing of the present invention.
Figure 7:
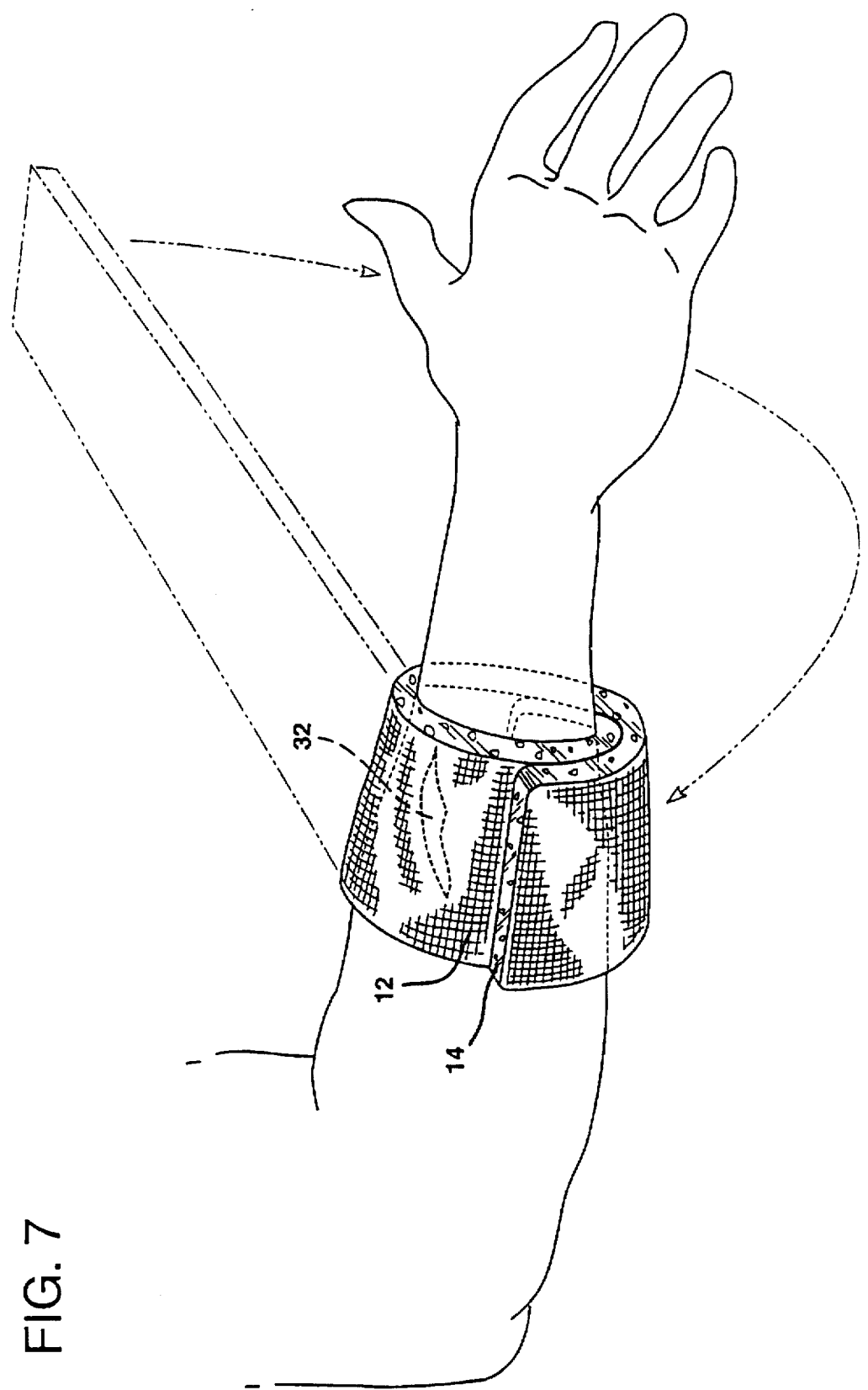

The wound dressing of the present invention is illustrated in FIGS. 1-5. Although the wound dressing is shown only in slightly elongated form, it should be appreciated that the wound dressing may be manufactured to be of any desired length so as to wrap around the desired portion of the patient's body, such as an arm, leg, etc. as shown in FIGS. 6 and 7.

Figure 1:
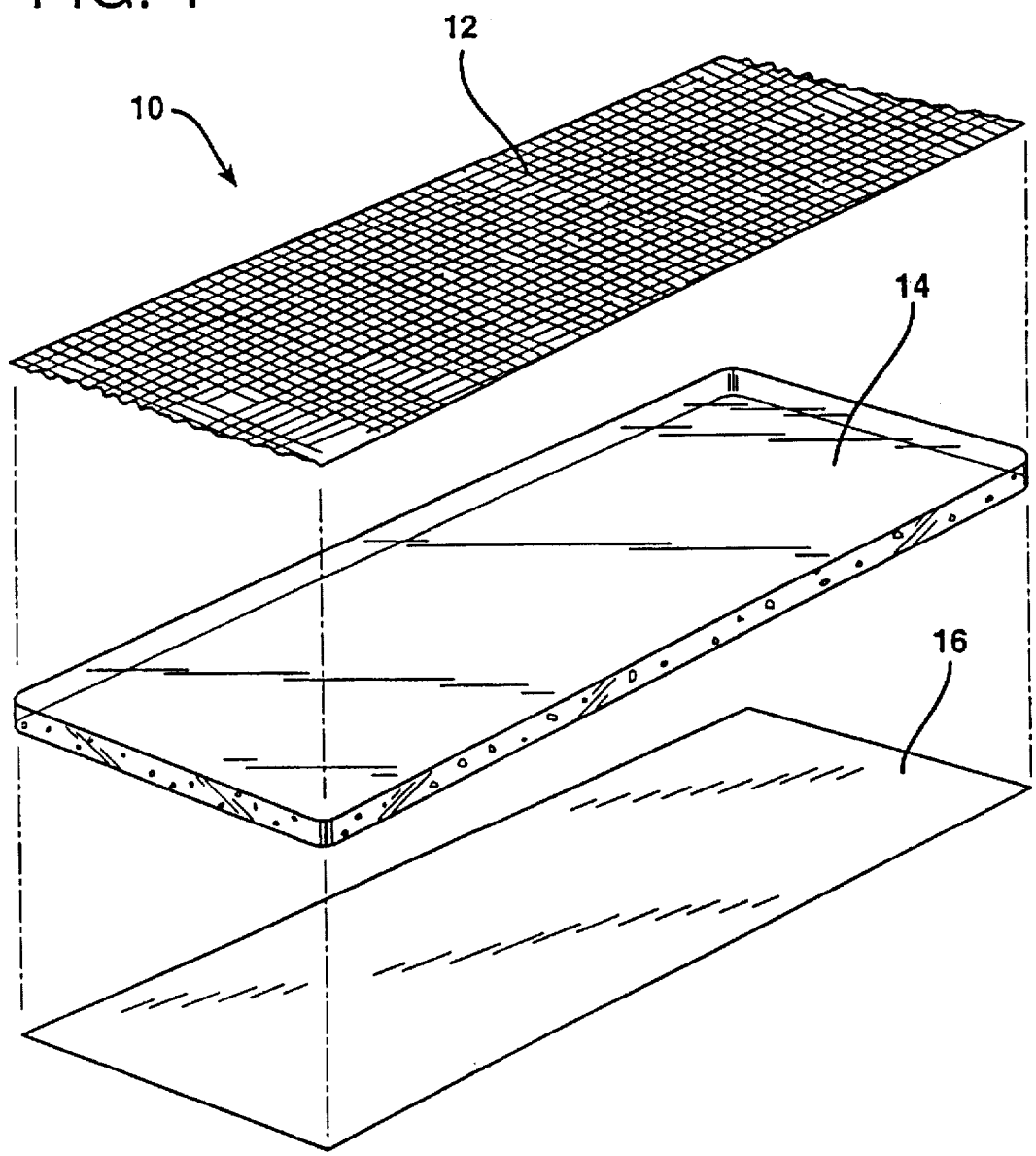
FIG. 1 is an exploded view of one embodiment of the wound dressing of the invention.

Referring, collectively, to FIGS. 1 and 4, the wound dressing 10 includes a vapor permeable bacterial barrier layer 12 having first and second sides 18 and 20, a hydrogel layer 14 having first and second sides 22 and 24, and an optional release liner 16. As shown, the first side 18 of the barrier layer 12 is adhered to the second side 24 of the hydrogel layer 14.

The vapor permeable bacterial barrier layer 12 is preferably formed of a material having sufficient porosity such that the barrier layer readily adheres to the hydrogel layer 14 without an adhesive. Materials commonly used in prior art wound dressings do not adhere directly to hydrogels, and thus, require an adhesive coating in order to provide a means by which additional support layers can be secured to the hydrogel layer. The bacterial barrier layer 12, however, possesses sufficient porosity so as to eliminate the necessity of an adhesive, thereby reducing the cost of manufacturing the wound dressing.

Preferably, the vapor permeable bacterial barrier layer is formed of a porous material comprising a foam material including silica and a polyolefin, where the porous material has a porosity ranging from about 30% to about 90%. The preferred porous material is a microporous synthetic sheet commercially available from PPG Industries, Inc. under the trademark Teslin®. The vapor permeable bacterial barrier layer readily permits the passage of air and water vapor while still minimizing bacterial proliferation in the wound.

The hydrogel material which forms layer 14 is preferably a saline solution in an aqueous gel-like phase. A preferred hydrogel material for use in the present invention in described in U.S. Pat. No. 5,423,737 issued Jun. 13, 1995, entitled HYDROGEL WOUND DRESSING WITH RELEASE TAB, the disclosure of which is hereby incorporated by reference. The gel-like consistency of the hydrogel material creates a bond with the wound site without creating an actual adhesive attachment that would damage new cell tissue upon removal. An advantage of the hydrogel layer is that it will not deteriorate as the wound fluids are absorbed. Additionally, it permits clean and neat removal of the wound dressing when the wound heals or the dressing is changed. An additional advantage of the hydrogel layer is that it is substantially transparent, making it possible to inspect the wound without removing the wound dressing.

As shown in FIG. 1, the wound dressing may further include a release liner 16, preferably silicone coated, which is secured to the first side of the hydrogel layer prior to use.

Figure 2:
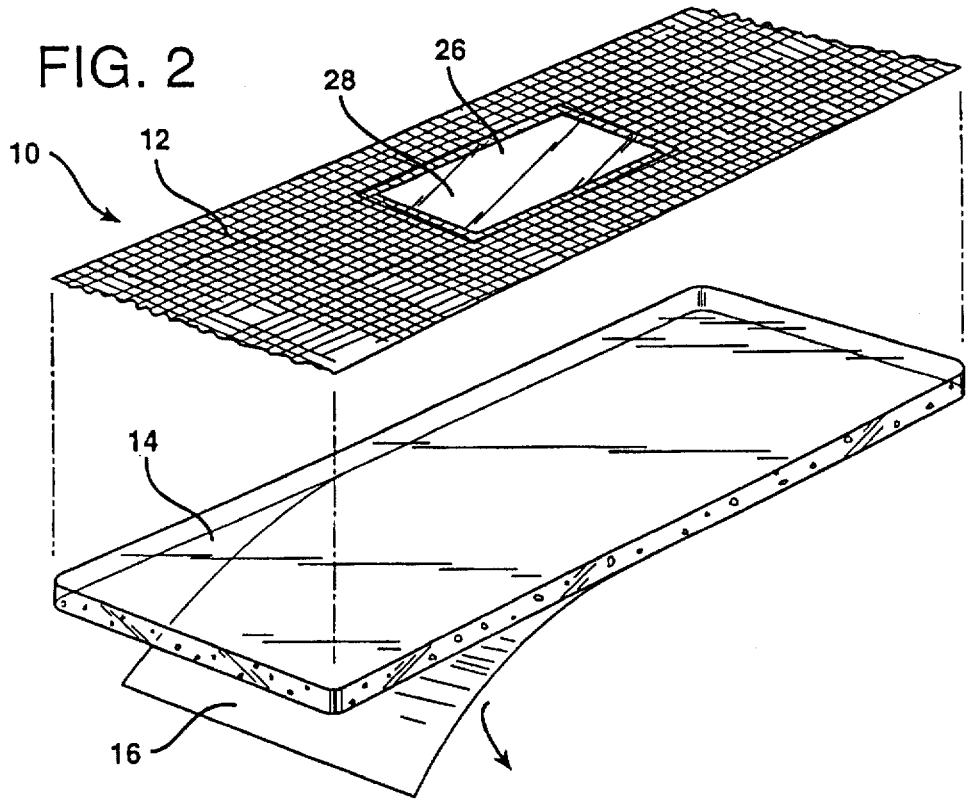
FIG. 2 is an exploded view of another embodiment of the invention.

FIG. 2 illustrates a preferred embodiment of the invention in which the vapor permeable bacterial barrier layer 12 includes an open area 26 therein comprising a window which is covered with a transparent film 28. While the window shown in FIG. 2 has a rectangular shape, it should be appreciated that the window may be any of a variety of desired shapes such as, for example, a circular window.

Because the hydrogel layer is substantially transparent, the use of a transparent film 28 over the open area 26 in the barrier layer allows medical personnel to monitor healing of the wound visually without removing the wound dressing. The transparent film also allows observation of an I.V. insertion site in applications where the wound dressing is used as an I.V. hold-down wrap.

Preferably, the transparent film comprises a thin-film polyurethane. As shown in FIG. 5, the film 28 is preferably adhered to the second side 20 of vapor permeable bacterial barrier layer 12 with a pressure sensitive adhesive 30.

Figure 3:
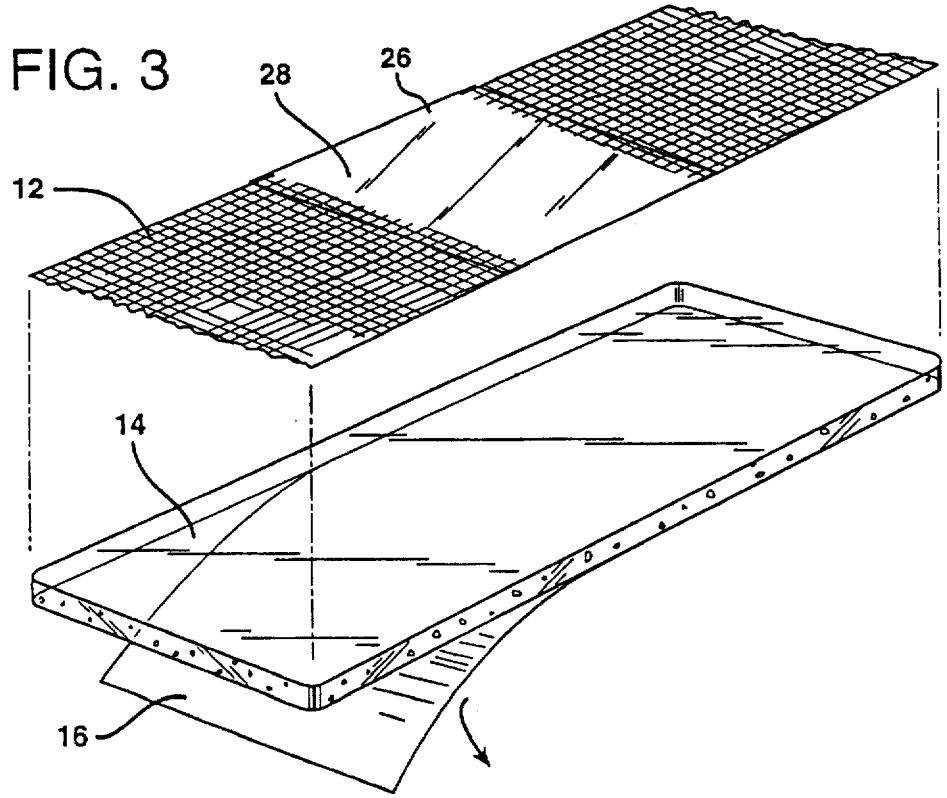
FIG. 3 is a exploded view of yet another embodiment of the invention.

FIG. 3 illustrates yet another embodiment of the invention in which the open area 26 in the barrier layer 12 comprises a gap which has been covered with a transparent film 28. As shown in FIG. 5, the transparent film includes a pressure sensitive adhesive 30 which adheres to the edges of the bacterial barrier layer.

FIGS. 6 and 7 illustrate the preferred method of applying the elongated wound dressing 10 to a patient having a wound 32, where the dressing includes first and second ends 34 and 36, and a center portion 38. As shown in FIG. 6, the release liner 16 is peeled from the wound dressing 10 such that the hydrogel layer 14 is exposed. The center portion 38 of the wound dressing is then applied to the wound 32 of the patient. The respective ends 34 and 36 of the wound dressing may then be gripped and wrapped around the patient. As shown in FIG. 7, the ends of the wound dressing are then overlapped such that the first surface of the hydrogel layer 14 contacts and adheres to the second surface of the vapor permeable bacterial barrier layer 12 so that the wound dressing is secured without the use of an adhesive.

With the wound dressing of the present invention, there is no portion of the patient's skin which is in contact with an adhesive. The hydrogel material does not adhere or stick to the wound, thereby allowing for easy removal of wound dressing 10 without destroying new cell tissue forming at the wound site. Additionally, the vapor permeable layer provides protection to the wound from bacterial proliferation. Thus, the wound dressing of the present invention provides a non-irritating, fluid absorbing, bacterial protective media over the wound site.

Further, the wound dressing can be manufactured at reduced cost as there are no adhesive layers or additional support layers required. A preferred method of manufacturing the wound dressing shown in FIG. 3 includes providing the vapor permeable bacterial barrier layer in the form of a continuous sheet having a gap along the length of its center portion and including a series of spaced apart cut lines along its width. A transparent film having a pressure sensitive adhesive on one side extends across the width of the gap and along the length of the continuous sheet so as to cover the gap. The resulting laminate structure is then processed through a gel coater to provide a hydrogel layer on the first side of the barrier layer. Individual wound dressings may then be separated from the laminate structure by cutting along the cut lines. Release liners may then applied to the hydrogel layer of each individual wound dressing.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. An elongated, self-adhesive wound dressing adapted to be wrapped around a portion of the patient's body so as to cover a wound, said wound dressing comprising:

a hydrogel layer having first and second sides, wherein said first side is adapted to contact the skin of a patient;

a vapor permeable bacterial barrier layer having a first side and a second side, wherein said first side of said barrier layer is secured to said second side of said hydrogel layer, said barrier layer formed of a porous material having sufficient porosity such that said hydrogel layer impregnates and adheres directly to said barrier layer without the use of an adhesive.

2. The wound dressing of claim 1 further comprising a release liner releasably secured to said first side of said hydrogel layer for protection of said hydrogel layer prior to use.

3. The wound dressing of claim 1 in which said vapor permeable barrier layer comprises a foam material comprising silica and a polyolefin.

4. The wound dressing of claim 1 in which said vapor permeable bacterial barrier material has a porosity in the range of from about 30% to about 90%.

5. The wound dressing of claim 1 in which said hydrogel is substantially transparent and said vapor permeable bacterial barrier layer comprises at least one open area therein such that a wound can be viewed through said open area and said hydrogel.

6. The wound dressing of claim 5 including a transparent film adhered to at least a portion of said second side of said vapor permeable bacterial barrier layer such that said open area is covered by said transparent film.

7. The wound dressing of claim 6 in which said transparent film is secured to said vapor permeable bacterial barrier layer with a pressure sensitive adhesive.

8. The wound dressing of claim 5 in which said open area comprises a window.

9. The wound dressing of claim 5 in which said open area comprises a gap in said barrier layer.

10. The wound dressing of claim 5 in which said transparent film comprises polyurethane.

11. A method of applying an elongated, self-adhering wound dressing to a wound comprising the steps of:

providing a wound dressing having first and second ends and a center portion, said wound dressing including a hydrogel layer having first and second sides wherein said first side is adapted to contact the skin of a patient, a vapor permeable bacterial barrier layer having a first side and a second side, said second side of said hydrogel layer impregnating and adhering directly to said first side of said barrier layer without the use of an adhesive; and a release liner releasably secured to said first surface of said hydrogel layer;

peeling said release liner from said wound dressing to expose said hydrogel and placing the center portion of said wound dressing on said wound such that said exposed hydrogel contacts said wound; and gripping the respective first and second ends of said wound dressing and wrapping said wound dressing around a portion of the patient's body such that said first surface of said hydrogel contacts and adheres to said second surface of said vapor permeable bacterial barrier layer, thereby maintaining said wound dressing in position over said wound.

* * * * *